United States Patent [19]

Makowka et al.

[11] Patent Number: 4,827,022
[45] Date of Patent: May 2, 1989

[54] PROCESS FOR THE PREPARATION OF DIMETHYLMALEATE

[75] Inventors: Bernd Makowka, Bergisch-Gladbach; Hans-Dieter Block, Leverkusen, both of Fed. Rep. of Germany

[73] Assignee: Bayer Aktiengesellschaft, Leverkusen, Fed. Rep. of Germany

[21] Appl. No.: 171,400

[22] Filed: Mar. 21, 1988

[30] Foreign Application Priority Data

Apr. 2, 1987 [DE] Fed. Rep. of Germany ....... 3711155

[51] Int. Cl.$^4$ .............................................. C07C 67/08
[52] U.S. Cl. ..................................... 560/204; 560/190
[58] Field of Search ......................................... 560/204

[56] References Cited

FOREIGN PATENT DOCUMENTS 0062874 10/1982 European Pat. Off. .
0976413 8/1983 Fed. Rep. of Germany .
0229117 10/1985 German Democratic Rep. .

OTHER PUBLICATIONS

Chem. Abstracts, 106: 119 301w, (1987).
Kirk–Othmer, Encyclopedia of Chemical Technology, Third Edition, John Wiley & Sons, New–York–Chichester–Brisbane–Toronto, vol. 7 (1979), pp. 870–875.
Kirk–Othmer, Encyclopedia of Chemical Technology, Third Edition, John Wiley & Sons, New–York–Chichester–Brisbane–Toronto, vol. 19 (1982), p. 886.
J. R. Fair, Chem. Eng. 74, pp. 67–74, Jul. (1967).
R. A. Mashelkar, Brit. Chem. Eng. 15, (10) pp. 1297–1304, Oct. (1970).

*Primary Examiner*—Werren B. Lone
*Assistant Examiner*—Vera C. Clarke
*Attorney, Agent, or Firm*—Connolly and Hutz

[57] ABSTRACT

An improved process for the preparation of dimethylmaleate by the esterification of maleic acid anhydride, maleic acid monomethylester, maleic acid or mixtures thereof with methanol in the presence of catalytic quantities of sulphuric acid, which comprises carrying out the esterification reaction within 20 to 120 minutes in a multistage bubble cap column reactor at temperatures of from 90° to 140° C. and with methanol excesses of from 0.4 to 2.0 mole per mole of the dimethylmaleate to be produced.

4 Claims, No Drawings

PROCESS FOR THE PREPARATION OF DIMETHYLMALEATE

This invention relates to a continuous process for the preparation of dimethylmaleate by the esterification of maleic acid anhydride, maleic acid, monomethylmaleate or mixtures thereof with methanol in the presence of catalytic quantities of sulphuric acid.

BACKGROUND OF THE INVENTION

Dimethylmaleate is a very versatile technical intermediate product which may be used, for example, as starting material for the copolymerisation with other vinyl compounds and as a precursor for pharmaceutical preparations and plant protective agents.

A known standard process for esterification is the reaction of an alcohol with an organic acid, usually in the presence of esterification catalysts which are generally inorganic acids or arylsulphonic acids. If the alcohols are low boiling, such as methanol or ethanol, the esterification reaction progresses only slowly, mainly due to the difficulty of removing the water of reaction from the mixture. It is for the same reason that incompletely reacted reaction mixtures usually containing high proportions of monoesters are obtained in the esterification of dicarboxylic acids.

It has frequently been attempted to overcome these difficulties by using a very large excess of alcohol but this lowers the reaction temperature and reaction velocity to an extent which is economically undesirable. It is also customary to use water-carrying auxiliary substances in esterifications, but these are difficult to use in the special case of methanol as its boiling point is too low.

A process for the continuous production of esters is described In British Patent Specification No. 732,784. In this process, numerous heating devices are used to maintain the esterification mixture at a temperature at which fractionation of the reactants will be substantially avoided.

British Patent Specification No. 1,430,069 discloses a process which overcomes the above-mentioned difficulties for a large number of high boiling carboxylic acids and in which esters of high boiling organic acids with readily volatile alcohols are prepared in the presence of an esterification catalyst by introducing an excess of the alcohol into a solvent-free carboxylic acid melt and removing the water of reaction from the reaction mixture in the form of steam until the reaction mixture has substantially completely esterified and is substantially free from water and alcohol. This single stage, batch-wise process which provides conversion rates in the region of 90%, based on the quantity of acid, is carried out at high temperatures which in the case of dimethylmaleate, for example, results in extensive transposition reactions to form dimethylfumarate, which is not wanted as reaction product.

By a more recent process described in German Patent Specification No. 3,114,320, maleic acid esters of short chained alcohols are also available. In this process, maleic acid, maleic acid anhydride or mixtures thereof with an excess of up to 300% of a readily volatile alcohol are reacted together under pressure to form dialkylmaleate. If the reaction temperatures employed are from 60 to 100 deg. Cent. above the boiling point of the alcohol put into the process, times of up to 19 hours are required for complete esterification. Under these conditions, the crude dialkylmaleate obtained has a fumaric ester content of up to 4% by weight, which is undesirable for many applications.

A mixture of 96% by weight of maleic acid dimethylester and 4% by weight of fumaric acid dimethylester, for example, has a melting point of about 25° C. and is therefore technically more difficult to handle than pure dimethylmaleate (storage, effort required for pumping). Furthermore, these fumaric ester components may lead to undesirable side products as a result of secondary reactions which is a particularly serious disadvantage in view of the great importance of this maleic acid ester as intermediate product.

BRIEF DESCRIPTION OF THE INVENTION

It has now surprisingly been found that dimethyl maleate is obtained in high yields within a short time and with a dimethylfumarate content of less than 1% by weight if the esterification reaction is carried out within 20 to 120 minutes at atmospheric pressure and relatively low temperatures.

DETAILED DESCRIPTION OF THE INVENTION

The process according to the invention for the preparation of dimethylmaleate from maleic acid, maleic acid anhydride, maleic acid monomethylester or mixtures thereof with methanol in the presence of catalytic quantities of sulphuric acid is characterised in that the esterification is carried out continuously in a bubble cap column with a methanol excess of from 0.4 to 2.0 mol of methanol per mol of the dimethylmaleate to be produced, the reaction being carried out for 20 to 120 minutes at reaction temperatures of from 90° to 140° C. under normal pressure, the methanol being passed through the bubble cap column from below either partly or completely in the gaseous form while the reaction mixture of dimethylmaleate, monomethylmaleate, maleic acid anhydride and an approximately stoichiometric quantity of methanol as well as catalyst is passed through the reactor from above. The alcohol is preferably used in an excess of from 50 to 100%, based on the stoichiometric proportions, and residence times of from 40 to 60 minutes are observed.

Very much shorter reaction times and lower fumaric acid ester contents are achieved in the process according to the invention than could be expected from the present state of the art.

In the process according to this invention, the esterification mixture is continuously passed through several reaction zones of the bubble cap column reactor until the mixture is free from water. A mixture of dimethylmaleate and a certain quantity of dissolved methanol (2–4% by weight) is removed from the reactor.

The term "bubble cap column reactor" is used to denote contact apparatus such as those described, for example, in 1. "Reaktionstechnik in Blasensäulen", Wolf-Dieter Deckwer, Verlag Salle/Sauerländer, 1985,
2. F. J. Brück and H. Hammer, Chem. Ing. Techn. 58, Heft 1 (1986); Chem. Ing. Techn. MS 1432/86,
3. Ullmanns Encyklopädie der techn. Chemie, Volume 3, Verfahrenstechnik II und Reaktionsapparate, Verlag Chemie, Weinheim/Bergstrasse 1973, p. 369–372,
4. J. R. Fair, Chem. Eng. 74, July 3, 67–74 (1967),
5. R. A. Mashelkar, Brit. Chem. Eng. 15, (10) 1297–1304 (1970), 6. Kirk-Othmer, Encyclopedia of chemical technology, Third Edition, John Wiley & Sons, New-York-Chichester-Brisbane-Toronto
   (a) Volume 7 (1979) page 870-875.
   (b) Volume 19 (1982) page 886.

In the process according to this invention, heating of the individual reaction zones by independent heating devices to a predetermined temperature to avoid fractionation of the reactants as far as possible is quite unnecessary. In fact, the heating devices are simply connected together and the only conditions to be observed are the obvious ones that the source of heating must be at a higher temperature than the reaction medium and that the quantity of heat supplied must be sufficient for evaporating the water of reaction and most of the excess methanol but not for evaporating the major proportion of the dimethylmaleate produced. This requirement is fulfilled most simply and reliably by using heating apparatus charged with steam under pressure.

According to this invention, an approximately stoichiometric mixture of maleic acid anhydride, maleic acid and/or monomethylmaleate and methanol as well as catalytic quantities of sulphuric acid, based on the above-mentioned reaction mixture, generally from 0.1 to 1% by weight, is introduced into the uppermost reaction stage of a bubble column.

A 50-100% molar excess, based on the maleic acid component put into the process, of methanol vapour which flows in countercurrent to the esterification mixture leaving the apparatus, is produced by the introduction of liquid or gaseous methanol in the lowest stage. A temperature profile with temperature values of from 90° C. to 140° C. forms along the column.

The individual values become established according to the temperature of the source of heating and the heat exchange surface and the quantity of material to be heated or evaporated. The water of reaction and small quantities of evaporated dimethylmaleate are driven off at the top with excess methanol vapour. The mixture of dimethylmaleate, methanol and catalyst acid removed from the lowermost reaction zone is worked up by distillation and the catalyst in the mixture is returned to the reaction with a proportion of ester obtained as product.

The advantages of the process lie in the low fumaric acid ester concentrations obtainable combined with high conversion rates within comparatively short esterification times and with little technical expenditure. Since the catalyst acid can be recovered and all valuable products can be returned, no contaminated effluent or exhaust gases are formed; this is to be regarded as another advantage of the process.

The preparation of dimethylmaleate according to this invention is explained in more detail in the following Examples (percentage figures denote percentages by weight unless otherwise indicated).

EXAMPLE 1

The esterification apparatus consists of a four-stage bubble cap column of glass having an internal diameter of 100 mm and a total height of 1800 mm. The height of bubbling in the individual reaction zones which are equipped with steam heating coils is 200 mm.

5.54 kg/h of maleic acid anhydride, 3.68 kg/h of methanol and 0.06 kg/h of 98% sulphuric acid are introduced into the uppermost stage of the reactor. The molar ratio of maleic acid anhydride to methanol is 1:2.03 and the catalyst concentration is 0.6% by weight. 2.8 kg/h of externally evaporated methanol are introduced into the lowest stage. The total quantity of alcohol put into the process is 80% above the stoichiometrically required quantity. The reaction temperature in the reaction zones is from 100° to 125° C. and the residence time of the esterification mixture in the reactor is approximately 45 minutes.

The ester product discharged from the lowermost stage has the following average composition:
96.5% dimethylmaleate
0.7% sulphuric acid
0.3% dimethylfumarate
2.5% methanol.

The steam mixture driven off overhead has the following composition:
55% methanol
26% water
19% dimethylmaleate.

TABLE II

The reactions described in Examples 2 to 7 were carried out in the apparatus described in Example 1 and are represented below in tabular form for the sake of clarity.

| Example[a] No. | kg/h MSA | kg/h(fl.) CH$_3$OH | Excess[b] CH$_3$OH based on MDE | Temp. range | Residence time in minutes | Conversion rate | FDE[c] content based on MDE |
|---|---|---|---|---|---|---|---|
| 2 | 6.17 | 4.03 | 66% | 92-98° C. | 40 | 99% | 0.1% |
| 3 | 10.98 | 7.23 | 45% | 90-100° C. | 25 | 95% | 0.1% |
| 4 | 4.12 | 2.69 | 100% | 98-109° C. | 60 | 100% | 0.2% |
| 5 | 3.33 | 0 | 150% | 93-110° C. | >60 | 100% | 0.3% |
| 6 | 4.12 | 2.69 | 150% | 90-98° C. | 60 | 98% | 0.1% |
| 7 | 6.17 | 4.03 | 33% | 100-115° C. | 40 | 96% | 0.4% |

[a]The quantity of sulphuric acid was in each case 0.5 ml of H$_2$SO$_4$/mol MSA
[b]Excess = quantity introduced as vapour
[c]in the discharge from the bubble cap column
MSA = maleic acid anhydride
MDE = dimethylmaleate
FDE = dimethylfumarate

What is claimed is:

1. In an improved process for the preparation of dimethylmaleate by the esterification of maleic acid anhydride, maleic acid monomethylester, maleic acid or mixtures thereof with methanol in the presence of catalytic quantities of sulphuric acid, the improvement comprises carrying out the esterification reaction within 20 to 120 minutes in a multistage bubble cap column reactor at temperatures of from 90° to 140° C. and with methanol excesses above the stoichiometric amount required of from 0.4 to 2.0 mol per mol of the dimethylmaleate to be produced.

2. Process according to claim 1 wherein the methanol excess amounts to 0.5 to 1.0 mol and the esterification time is from 40 to 60 minutes.

3. Process according to claim 1 wherein the pressure of the esterification reaction is about atmospheric pressure.

4. Process according to claim 1 wherein the bubble cap column reactor has four stages.

* * * * *